US00PP21718P2

(12) United States Plant Patent
McGranahan et al.

(10) Patent No.: US PP21,718 P2
(45) Date of Patent: Feb. 22, 2011

(54) WALNUT TREE NAMED 'IVANHOE'

(50) Latin Name: *Juglans regia*
Varietal Denomination: Ivanhoe

(75) Inventors: Gale McGranahan, Davis, CA (US); Charles Leslie, Davis, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 12/653,141

(22) Filed: Dec. 8, 2009

(51) Int. Cl.
*A01H 5/00* (2006.01)

(52) U.S. Cl. ..... Plt./154

(58) Field of Classification Search ..... Plt./154
See application file for complete search history.

(56) References Cited

PUBLICATIONS

The Apr. 26, 2005 Test Agreement For Trees between Golden Valley Nursery and The Regents Of The University of California, 8 pages.
The Aug. 22, 2002 Test Agreement For Trees between David Scheuring and The Regents Of The University of California, 6 pages.
The Dec. 12, 2002 Test Agreement For Trees between Alfred Bonturi and The Regents Of The University of California, 6 pages.
The Feb. 1, 2008 Test Agreement For Trees between Stuke nursery Co. Inc. and The Regents Of the University of California, 7 pages.
The Feb. 1, 2009 Test Agreement For Trees between Green Tree Nursery and The Regents Of The University of California, 7 pages.
The Feb. 1, 2009 Test Agreement For Trees between Miya Farms, Inc. and The Regents Of The University of California, 7 pages.
The Feb. 1, 2009 Test Agreement For Trees between The Burchell Nursery, Inc. and The Regents Of The University of California, 7 pages.
The Feb. 20, 2007 Test Agreement For Trees between FDS Farms and The Regents Of The University of California, 7 pages.
The Mar. 1, 2003 Test Agreement For Trees between David Scheuring and The Regents Of The University of California, 8 pages.
The Mar. 1, 2006 Test Agreement For Trees between Carriere & Sons and The Regents Of The University of California, 7 pages.
The Mar. 1, 2007 Test Agreement For Trees between Carriere & Sons and The Regents Of The University of California, 7 pages.
The Mar. 1, 2007 Test Agreement For Trees between Deardorff Farms Management, Inc. and The Regents Of The University of California, 7 pages.
The Mar. 1, 2007 Test Agreement For Trees between Whitney Warren Ranch and The Regents Of The University of California, 7 pages.
The Mar. 1, 2008 Test Agreement For Trees between The Burchell Nursery, Inc. and The Regents Of The University of California, 7 pages.
The Mar. 11, 2003 Test Agreement For Trees between Sierra Gold Nursery and The Regents Of The University of California, 7 pages.
The Mar. 19, 2003 Test Agreement For Trees between Jerry Moore and The Regents Of The University of California, 6 pages.
The Mar. 24, 2006 Test Agreement For Trees between Walter Deardorff and The Regents Of The University of California, 8 pages.
The Sep. 1, 2002 Test Agreement For Trees between Driver Nursery, Inc. and The Regents Of The University of California, 5 pages.
The Sep. 1, 2008 Test Agreement For Trees between The Burchell Nursery, Inc. and The Regents Of The University of California, 7 pages.

*Primary Examiner*—Annette H Para
(74) *Attorney, Agent, or Firm*—Morrison & Foerster LLP

(57) ABSTRACT

A new and distinct variety of walnut tree denominated 'Ivanhoe' is described. This new variety, 'Ivanhoe', comes into bearing young, with an excellent yield. 'Ivanhoe' forms large-sized walnuts that possess light-colored kernels with little size variation in a given harvest. 'Ivanhoe' bears fruit terminally and laterally and yields a crop that can be harvested approximately 4 weeks before 'Chandler' (U.S. Plant Pat. No. 4,388). 'Ivanhoe' is also protogynous, bearing female flowers before male flowers.

9 Drawing Sheets

Latin name: Botanical/commercial classification: (*Juglans regia*)/new English walnut tree cultivar.

Varietal denomination: The varietal denomination of the claimed walnut is 'Ivanhoe'.

BACKGROUND OF INVENTION

The present invention relates to a new and distinct cultivar of walnut tree (*Juglans regia*) that has been denominated as 'Ivanhoe' and more particularly to a walnut tree that has a harvest date approximately 4 weeks earlier than the walnut tree cultivar 'Chandler' (U.S. Plant Pat. No. 4,388), and that further produces a walnut that is large in size with very light colored kernels.

It has long been recognized as desirable to provide walnut trees bearing large crops that are ripe for commercial harvesting and shipment early in the harvest season. The tree of the present cultivar, 'Ivanhoe' produces a nut that has a quality similar to the highest quality cultivar 'Chandler' (U.S. Plant Pat. No. 4,388), however the new cultivar is ready for harvest approximately 4 weeks before 'Chandler,' about the same time as the reference cultivar 'Payne' (old cultivar; not patented).

The new *Juglans regia* walnut tree of the present invention was created at Davis, Calif. in 1995 by a controlled pollination between the cultivar 'Chico' and 'UC67-13' (neither patented). The pedigree is illustrated (FIG. 1).

Seeds from the cross were planted and the resulting 27 trees were carefully observed along with other trees in the walnut breeding program. When they began to bear nuts, data were collected annually on leafing date; first, peak, and last female flower bloom; first, peak; and last male bloom; blight severity; and yield (Table 1). Nuts were sampled and cracked, and data were collected on shell appearance, shell thickness, shell integrity, shell strength, nut weight, kernel weight, percent kernel, ease of kernel removal, kernel color, and percent kernel shrivel (Table 1). A single tree was selected from among progeny of this controlled cross based on its superior attributes. This selection was originally designated 'UC95-11-14' and is now designated as the 'Ivanhoe' cultivar, after the town in California where it performed in a superior manner. Compared to 'Ivanhoe', the parent 'UC67-13' is protandrous, has larger nuts, a slightly later harvesting date, and is susceptible to pistillate flower abscission; the parent 'Chico' has smaller nuts than 'Ivanhoe' with a more difficult to extract kernel.

The new 'Ivanhoe' cultivar of the present invention has been asexually reproduced by grafting at Davis, Calif. on 'Paradox' rootstock. The distinctive characteristics of the new cultivar have been found to be stable and are transmitted to the new trees when asexually propagated.

SUMMARY OF THE INVENTION

It was found that the walnut cultivar 'Ivanhoe' of the present invention exhibits the following combination of characteristics:

a) comes into bearing young, with an excellent yield;
b) forms large-sized walnuts that possess light-colored kernels with little size variation in a given harvest;
c) bears fruit terminally and laterally;
d) yields a crop that can be harvested approximately 4 weeks before 'Chandler' (U.S. Plant Pat. No. 4,388); and
e) is protogynous, bearing female flowers before male flowers.

BRIEF DESCRIPTION OF THE TABLE

Table 1 shows tree and nut evaluations for both parents and the most common walnut cultivar 'Chandler'.

BOTANICAL DESCRIPTION OF THE PLANT

The description is based on an ungrafted walnut tree on its own roots and trees subsequently grafted on 'Paradox' rootstock growing in an orchard in Davis, Calif., in selection blocks in Chico, Calif., and Parlier, Calif.; as well as in grower trials near Yuba City, Calif., near Madison, Calif., and near Ivanhoe, Calif. The first data were collected on the own rooted tree from 1999 at age 3 years, to 2005, age 9. Data from 2004 to 2008 were collected from grafted trees.

The Munsell Book of Color is used in the identification of color. Also, common color terms are to be accorded their ordinary dictionary significance.

Botanical classification: *Juglans regia.*

*Female parent.*—'UC67-13'.

Figure 1:
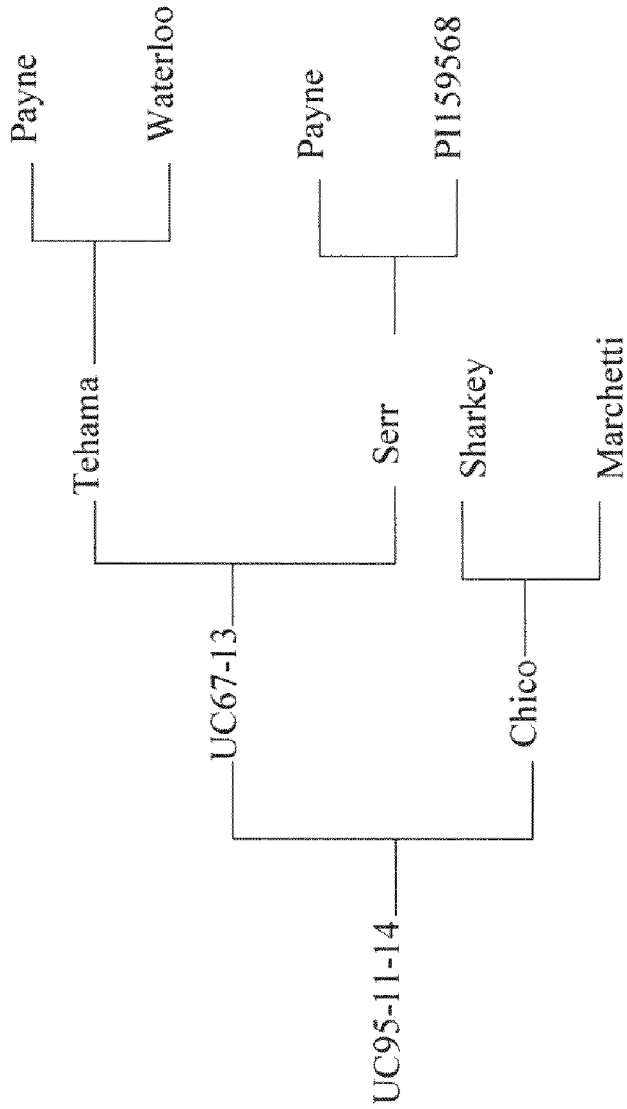
FIG. 1 shows pedigree of the 'Ivanhoe' walnut.

*Male parent.*—'Chico'. The pedigree is shown (FIG. 1).

Figure 2:
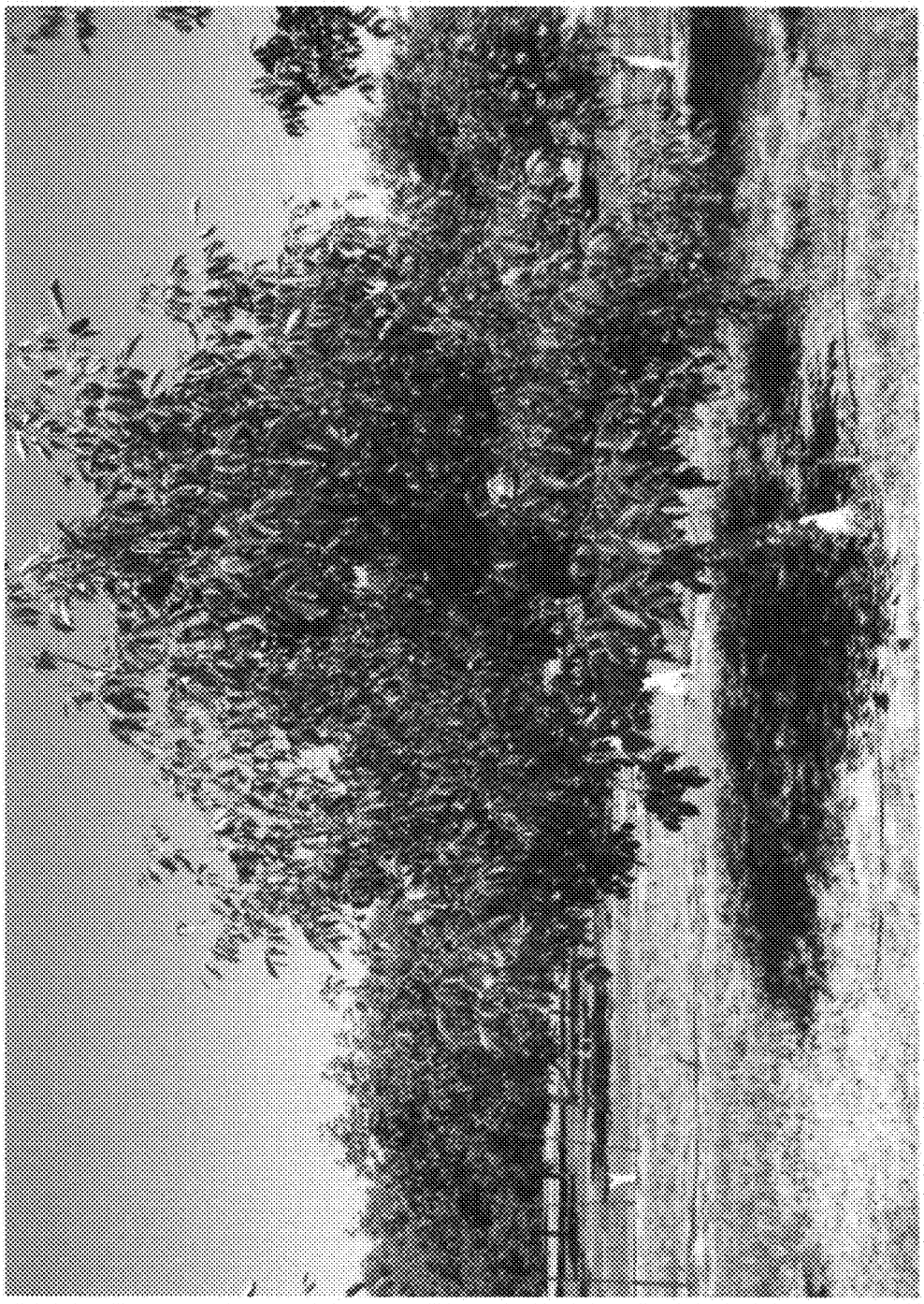
FIG. 2 shows a tree of 'Ivanhoe' walnut at 7 years.
Figure 3:
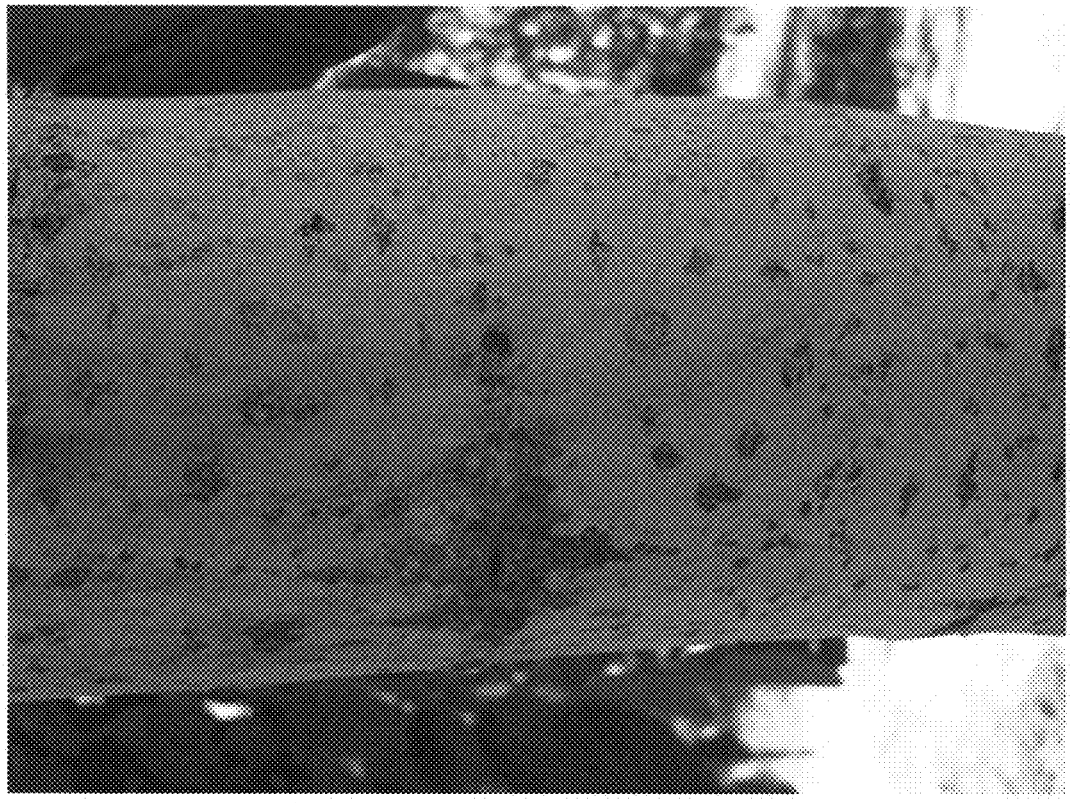
FIG. 3 shows bark of 'Ivanhoe' walnut.

Plant: The growth habit of the plant is illustrated in FIG. 2. This 7 year old tree is approximately 5.2 m in height with a canopy diameter of 6.4 meters. The trunk diameter at 1.2 meters above the ground is approximately 10 cm. The silvery grey bark is typical of *Juglans regia.* The young bark is brown (2.9GY 2.3/3.6) and the older bark is grey (5Y 7.5/2) with raised lighter lenticels (2.5Y 8/2) (FIG. 3). Lenticels are round to oval in shape, 1-10 mm×1-3 mm in size. 'Ivanhoe' has a vigor similar to 'Chandler'.

Figure 4:
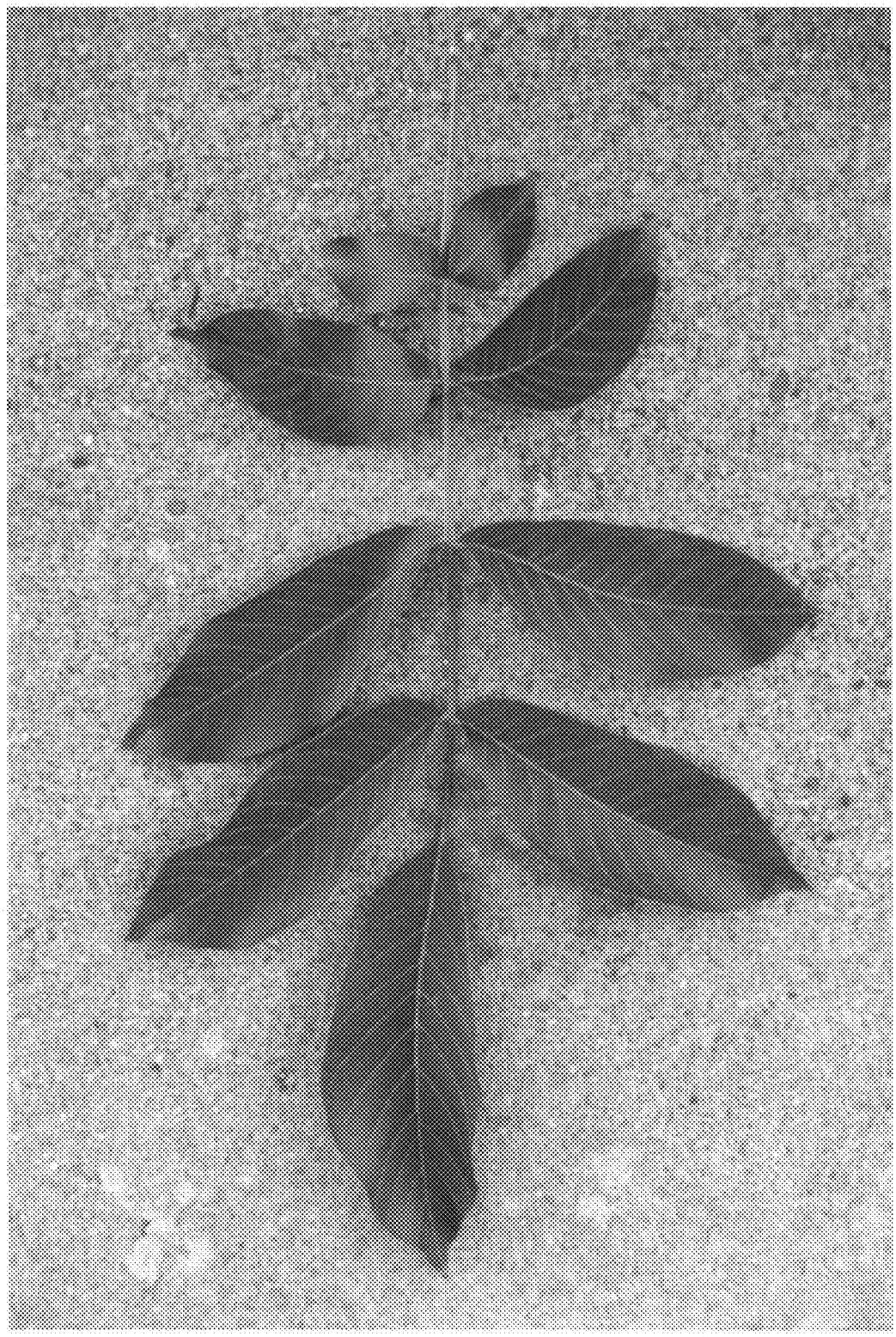
FIG. 4 shows adaxial view of leaf of 'Ivanhoe' walnut.
Figure 5:
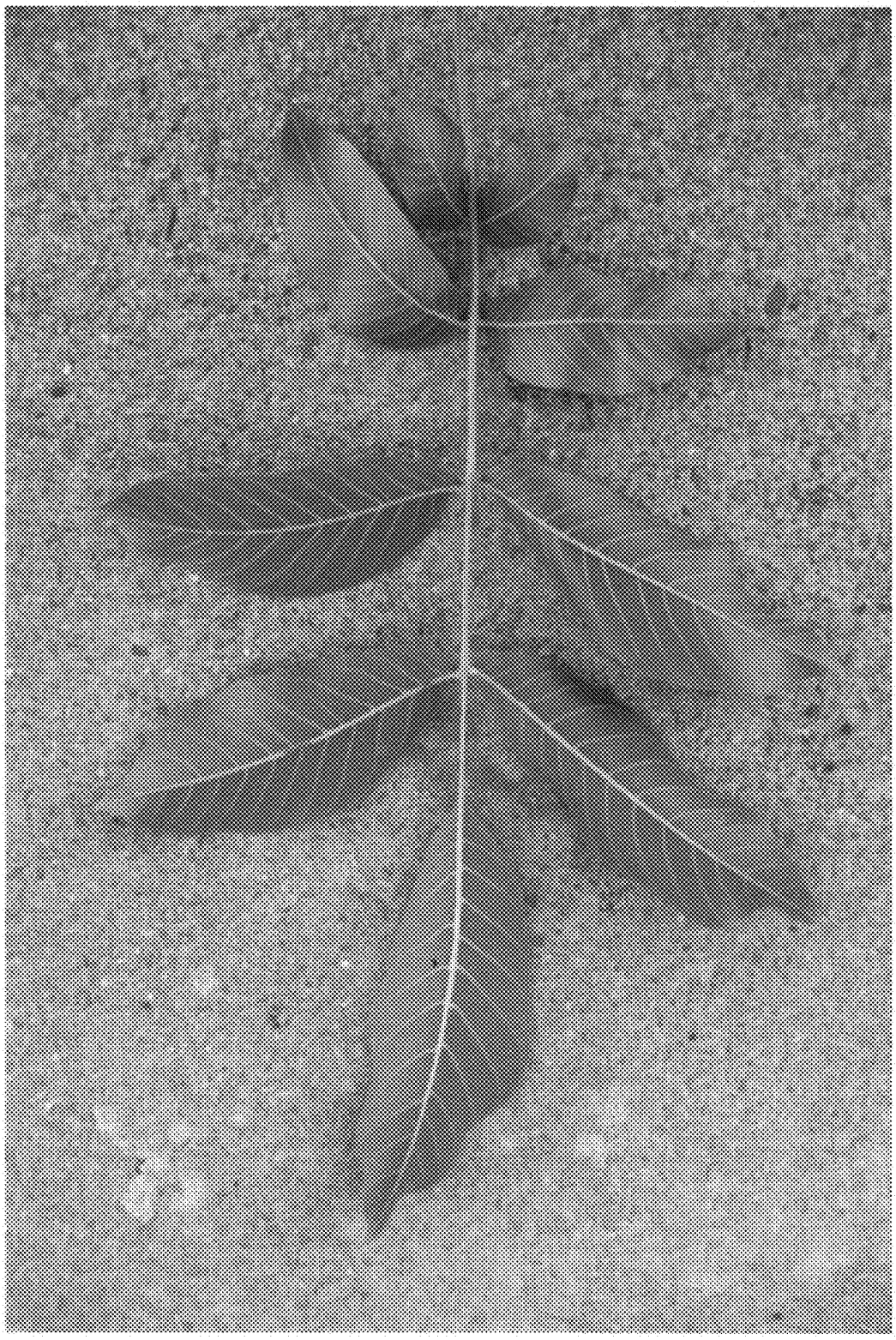
FIG. 5 shows abaxial view of leaf of 'Ivanhoe' walnut.

Foliage: The dark green foliage is illustrated in FIG. 4 and FIG. 5 and is typical of *Juglans regia.* Leafing out date between 1999 and 2008 has occurred on March 19$^{th}$ on the average. For comparative purposes the 'Chandler' cultivar leaf-out is April 3$^{rd}$. The typical leaf coloration is green (adaxial 5GY 4/4, abaxial 5GY 8/2) The leaves are pinnately compound with 7-9 leaflets. The full leaf length is approximately 40 cm and width is 29 cm. Leaflets are broadly elliptical and entire. The terminal leaflet averages 16 cm in length and 8 cm in width. The middle leaflets average 15 cm in length and 6 cm in width and the proximal leaflets average 6 cm in length and 3 cm in width. The rachis averages 23 cm in length and 2-4 mm in diameter. Petiole length is 8 cm and is 5GY 7/8 in color.

Figure 6:
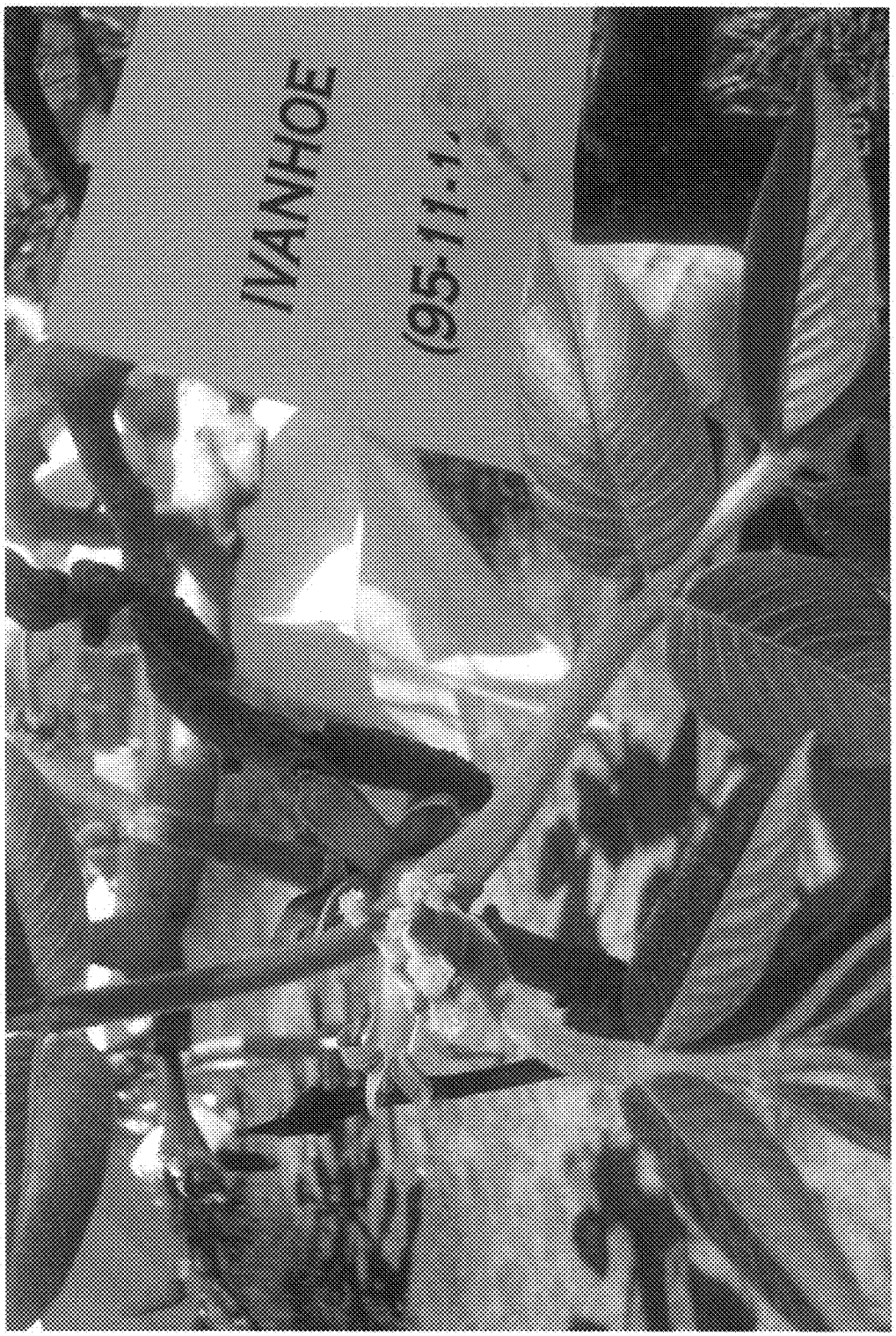
FIG. 6 shows female flowers of 'Ivanhoe' walnut.
Figure 7:
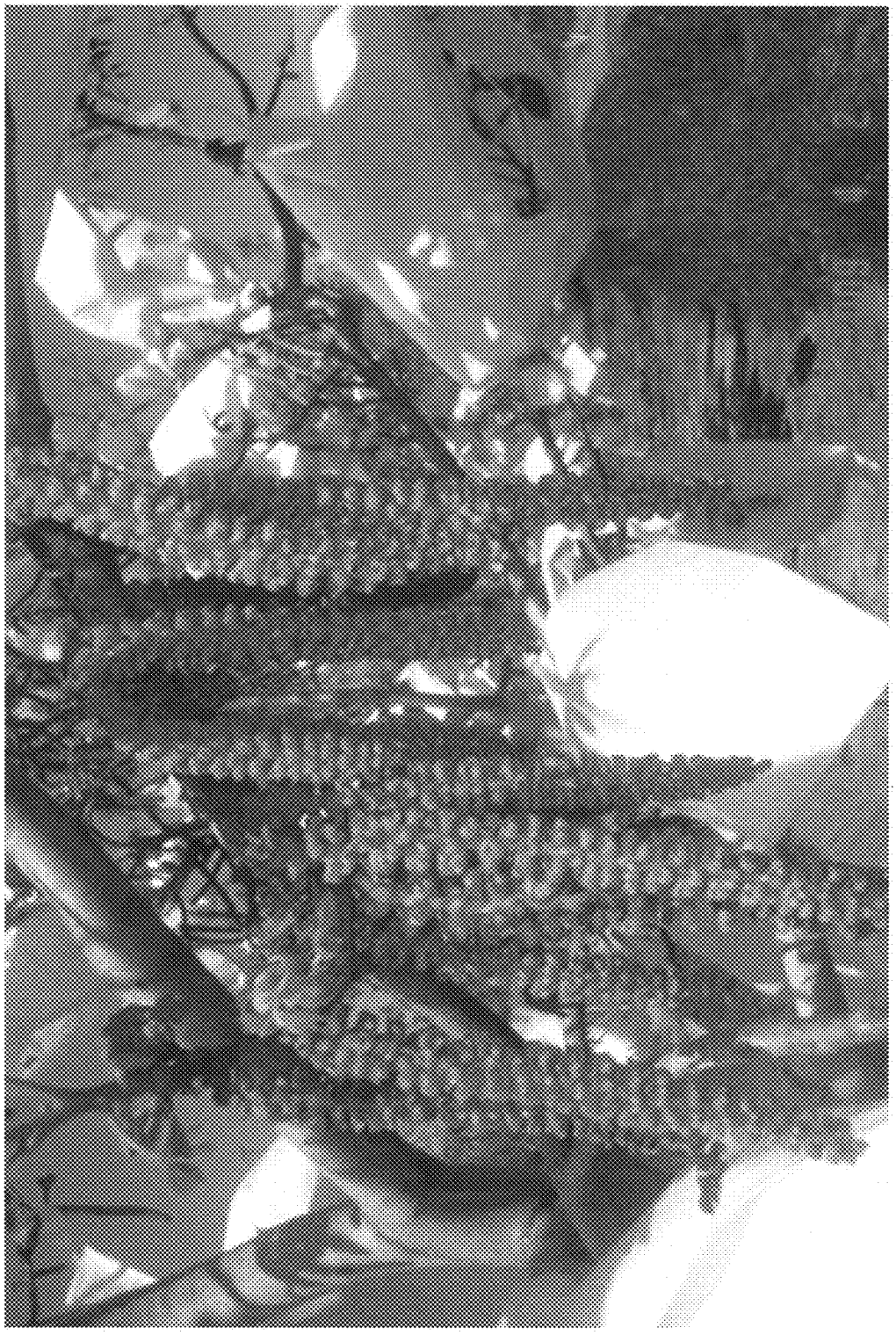
FIG. 7 shows catkins (male flowers) of 'Ivanhoe' walnut.

Inflorescence: The tree is precocious with excellent yield being noted at age 3 years. Male flowers (catkins) were not present until age 5 years. This delay in male maturity is typical of *Juglans regia.* From 1999 to 2008, average first female bloom occurred on March 23, peak bloom on March 28, and last bloom on April 3. From 2001 to 2008, average male flowering (pollen shedding) began April 1, peaked on April 8, and terminated April 15. In this protogynous tree, pollen shedding does not completely cover pistillate bloom suggesting that a pollenizer would be needed for maximum yield in isolated areas. 'Sexton' (U.S. Plant Pat. No. 16,496P3), 'Payne' (unpatented), and 'Serr' (unpatented) would be satisfactory pollenizers. The female flowers are typical of *Juglans regia* (FIG. 6) with 2-3 flowers per inflorescence borne on 1 cm spike at both terminal and lateral positions on current season's growth. Approximately 100% of the lateral buds contain inflorescences making yields much greater than trees that only bear flowers terminally. A typical female flower is approximately 5 to 7 mm at anthesis and floral organs are typical of *Juglans regia.* The flowers appear vase-shaped when the 2 plumose stigmatic arms are curved outward. There are no petals. The female flowers are green (5GY 7/8) in color. The flower fragrance is typical of *Juglans regia* and is not noticeably different than the foliage fragrance. The male flowers (FIG. 7) are borne on catkins, between 7 and 13 cm in length and 1.5 cm in diameter, and are green in color (5GY 7/8).

Figure 8:
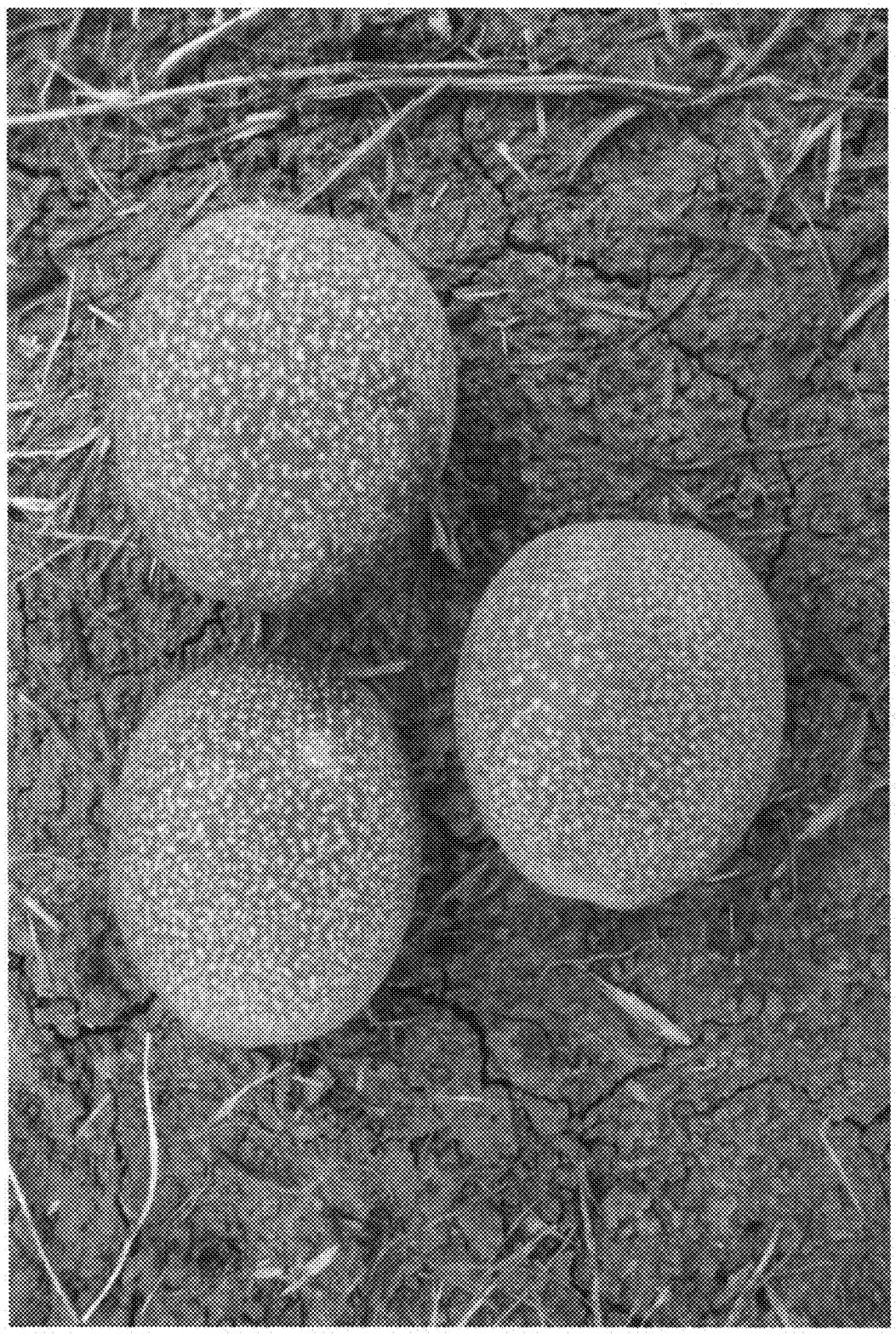
FIG. 8 shows hulls of 'Ivanhoe' walnut.
Figure 9:
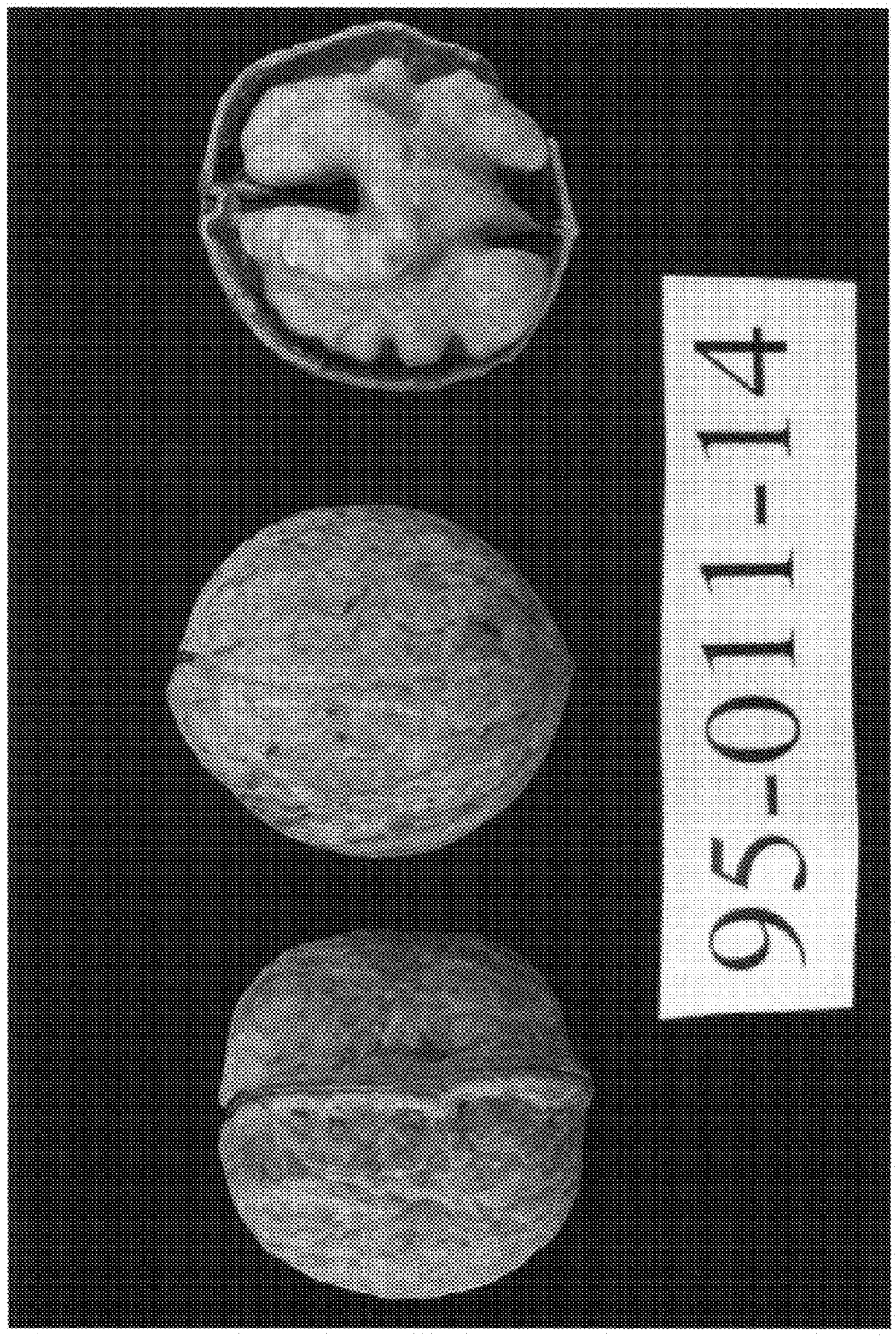
FIG. 9 shows nut and kernel of 'Ivanhoe' walnut.

Walnuts: The new cultivar commonly harvests about 4 weeks before 'Chandler' and about 3 days before 'Payne'. The new cultivar has excellent yields of mostly large-sized walnuts. The hull is globose, 4.8 cm×4.5 cm, 3 mm thick and 5GY 6/4 in color with numerous lighter speckles (FIG. 8). The nut is broadly elliptical, very smooth, tan (7.5YR 8/2) and measures approximately 40 mm in length and 35 mm in width (FIG. 9). The shell is 1.5 mm thick, relatively strong and well sealed and the kernel is easy to remove. The kernel weight averages 7.7 g and makes up 57% of the total nut weight of 13.5 g. Kernel color is considered excellent and scores mostly in the light to extra light categories of the USDA Standards for Grades of Shelled Walnuts as determined by using the standard Walnut Color Chart for kernels published by the Dried Fruit Association of California. In addition kernels of 'Ivanhoe' scored 53 on the Relative Light Index used by Diamond Foods of Stockton, Calif. It is typical of commercial walnuts in terms of flavor and firmness, the latter varying according to the percent moisture after drying.

Disease susceptibility: Blight caused by *Xanthomonas campestris* pv. *juglandis* can be a problem on this early leafing cultivar. It may also be susceptible to sunburn if the nuts are in exposed locations. Pistillate flower abscission has not been a problem.

Usage: This new cultivar of the present invention provides an early season walnut with high quality light-colored kernels that can be used cracked or in-shell.

TABLE 1

Performance of 'Ivanhoe' compared to its parents and 'Chandler'

| | Variety | | | |
|---|---|---|---|---|
| Trait[1] | Ivanhoe[2] | UC67-13[3] | Chico[4] | Chandler[5] |
| Leafing date | 19 Mar. | 23 Mar. | 22 Mar. | 3 Apr. |
| Pollen shed date | | | | |
| First | 1 Apr. | 30 Mar. | 6 Apr. | 4 Apr. |
| Peak | 8 Apr. | 6 Apr. | 12 Apr. | 11 Apr. |
| Last | 15 Apr. | 19 Apr. | 20 Apr. | 20 Apr. |
| Female bloom date | | | | |
| First | 23 Mar. | 6-Apr. | 25 Mar. | 15 Apr. |
| Peak | 28 Mar. | 11 Apr. | 31 Mar. | 22 Apr. |
| Last | 3 Apr. | 19 Apr. | 9 Apr. | 29 Apr. |
| Harvest date | 13 Sep. | 19 Sep. | 17 Sep. | 7 Oct. |
| Catkin abundance | 5 | 6 | 5 | 5 |
| Female abundance | 7 | 6 | 6 | 6 |
| Flowers/inflorescence | 2 | 2 | 2 | 2 |
| Percent lateral bud fruitfulness | 100 | 96 | 100 | 95 |
| Yield | 7 | 6 | 6 | 6 |
| Shell | | | | |
| Texture | 4 | 5 | 4 | 5 |
| Color | 4 | 5 | 5 | 4 |
| Seal | 4 | 5 | 5 | 5 |
| Strength | 5 | 5 | 6 | 4 |
| Integrity | 7 | 7 | 7 | 7 |
| Thickness | 1.5 | 1.5 | 1.5 | 1.3 |
| Packing tissue | 5 | 5 | 6 | 5 |
| Kernel | | | | |
| Inshell weight | 13.5 | 15.2 | 11.4 | 13.5 |
| Kernel weight | 7.7 | 8.4 | 5.3 | 6.7 |
| Percent kernel | 57 | 56 | 47 | 50 |
| Fill | 5 | 5 | 6 | 5 |
| Plumpness | 5 | 5 | 5 | 4 |
| Ease of removal | 4 | 4 | 6 | 4 |
| Percent blank | 1 | 2 | 2 | 2 |
| Percent extra light | 38 | 21 | 9 | 49 |
| Percent light | 51 | 73 | 76 | 45 |

TABLE 1-continued

Performance of 'Ivanhoe' compared to its parents and 'Chandler'

| | | | | |
|---|---|---|---|---|
| Percent light amber | 10 | 4 | 12 | 5 |
| Percent amber | 1 | 2 | 3 | 0 |
| Percent tip shrivel | 1 | 0 | 0 | 28 |
| Percent veins | 10 | 45 | 19 | 18 |

KEY FOR TABLE 1

| | |
|---|---|
| Tree evaluation | |
| Catkin abundance | Male flower abundance: 3 low; 5 intermediate; 7 high |
| Female abundance | Female flower abundance: 3 low; 5 intermediate; 7 high |
| Lateral fruitfulness % | Percent of lateral buds with female flowers |
| Yield | Yield: 3 low; 5 intermediate; 7 high |
| Nut and kernel traits | |
| Texture | Shell texture: 3 smooth; 5 medium; 7 rough |
| Color | Shell color: 3 light; 5 medium; 7 dark |
| Seal | Shell seal: 3 weak; 5 intermediate; 7 strong |
| Strength | Shell strength: 3 weak; 5 intermediate; 7 strong |
| Integrity | Shell integrity: 3 substantial area of shell missing; 5 small area of missing shell; 6 stem end hole; 7 complete shell |
| Thickness | Shell thickness at mid-cheek in mm |
| Packing tissue | Inner lining: 3 thin; 5 medium; 7 thick |
| Inshell weight | g |
| Kernel weight | g |
| Kernel % | Kernel wt/inshell wt × 100 |
| Fill | Kernel fill: 3 poor; 5 moderate; 7 well |
| Plumpness | Kernel plumpness: 3 thin; 5 moderate; 7 plump |
| Ease of removal | Ease of removal of kernel halves: 3 easy; 5 moderate; 7 difficult |
| Blanks % | Percent of nuts without a kernel |
| Extra light % | Percent of kernels in extra light category (DFA) |
| Light % | Percent of kernels in light category (DFA) |
| Light amber % | Percent of kernels in light amber category (DFA) |
| Amber % | Percent of kernels in amber category (DFA) |
| Tip shrivel % | Percent of kernels with tip shrivel like Chandler |
| Veins % | Percent of kernels with conspicuous veins |

[1]See attached 2 for description of scores
[2]Data 2000-2008
[3]Data 1988-2002
[4]Data 1988-2003
[5]Data 1988-2008
DFA Dried Fruit Association of CA

What we claim is:

1. A new and distinct variety of walnut tree designated 'Ivanhoe' as shown and described herein.

* * * * *